US012702438B2

(12) United States Patent
Zhang

(10) Patent No.: US 12,702,438 B2
(45) Date of Patent: Aug. 11, 2026

(54) ULTRASONIC SCALPEL HANDLE

(71) Applicant: Ensurge Medical (Suzhou) Co., Ltd., Suzhou (CN)

(72) Inventor: Jun Zhang, Suzhou (CN)

(73) Assignee: Ensurge Medical (Suzhou) Co., Ltd., Suzhou (CN)

( * ) Notice: Subject to any disclaimer, the term of this patent is extended or adjusted under 35 U.S.C. 154(b) by 445 days.

(21) Appl. No.: 18/251,155

(22) PCT Filed: Oct. 22, 2021

(86) PCT No.: PCT/CN2021/125624
§ 371 (c)(1),
(2) Date: Apr. 28, 2023

(87) PCT Pub. No.: WO2022/095727
PCT Pub. Date: May 12, 2022

(65) Prior Publication Data

US 2023/0397927 A1 Dec. 14, 2023

(30) Foreign Application Priority Data

Nov. 4, 2020 (CN) ......................... 202011212999.8
Mar. 3, 2021 (CN) ......................... 202120458579.1
Jul. 5, 2021 (CN) ......................... 202110756263.5

(51) Int. Cl.
*A61B 17/3213* (2006.01)
*A61B 17/32* (2006.01)
*A61B 17/00* (2006.01)

(52) U.S. Cl.
CPC .. *A61B 17/3213* (2013.01); *A61B 17/320092* (2013.01); *A61B 2017/00367* (2013.01);
(Continued)

(58) Field of Classification Search
CPC ....... A61B 2017/320082; A61B 2017/320092; A61B 2017/320068; A61B 2017/320098;
(Continued)

(56) References Cited

U.S. PATENT DOCUMENTS 5,938,633 A * 8/1999 Beaupre ......... A61B 17/320068 604/22
6,623,500 B1 9/2003 Cook et al.
(Continued)

FOREIGN PATENT DOCUMENTS

CN 105939679 A 9/2016
CN 109044491 A 12/2018
(Continued)

OTHER PUBLICATIONS

Chinese Office Action issued for Chinese Patent Application No. 202110756263.5, dated Oct. 24, 2022 in 10 pages including English translation.

(Continued)

*Primary Examiner* — Brigid K Byrd
(74) *Attorney, Agent, or Firm* — Knobbe, Martens, Olson & Bear, LLP

(57) ABSTRACT

An ultrasonic scalpel handle, comprising a handle housing (11) and a transducer assembly (12). The transducer assembly (12) is integrally accommodated in the handle housing (11) and can rotate about its own axis. The transducer assembly (12) comprises a transducer shell (121) and a transducer (122) fixedly disposed to each other, and a conductive member (123) fixedly provided outside the transducer shell (121). The conductive member (123) has at least a conductive portion. The transducer (122) is fixedly and electrically connected to the conductive portion. An electric element (13) is further fixedly provided in the handle housing (11). In the process that the transducer assembly
(Continued)

(12) rotates about its own axis with respect to the handle housing (11), the electric element (13) is always in contact with the conductive portion to maintain electric connection. In this way, in the process that the transducer assembly rotates about its own axis in the handle housing, power cord does not rotate with it, and the power cord may further extend in the lower part of the handle, such that a series of problems of heavy burden on the arm and easy fatigue, and knotting of the power cord, etc. caused by the power cord extending from the rear portion of the handle housing are avoided.

6 Claims, 9 Drawing Sheets

(52) U.S. Cl.
CPC ................ *A61B 2017/0042* (2013.01); *A61B 2017/0046* (2013.01); *A61B 2017/320075* (2017.08); *A61B 2017/320082* (2017.08); *A61B 2017/320093* (2017.08)

(58) Field of Classification Search
CPC .... A61B 2017/320069; A61B 17/3213; A61B 2017/2929
See application file for complete search history.

(56) References Cited

U.S. PATENT DOCUMENTS

| | | | | |
|---|---|---|---|---|
| 7,476,233 | B1 | 1/2009 | Wiener et al. | |
| 9,427,249 | B2 * | 8/2016 | Robertson | A61B 17/3207 |
| 2015/0051516 | A1 * | 2/2015 | Sanai | A61B 17/320092 601/2 |
| 2016/0121143 | A1 * | 5/2016 | Mumaw | A61B 90/08 601/2 |
| 2018/0161815 | A1 * | 6/2018 | Kim | B06B 1/0611 |
| 2018/0221049 | A1 * | 8/2018 | Faller | A61B 17/320092 |

FOREIGN PATENT DOCUMENTS

| | | | |
|---|---|---|---|
| CN | 209404883 | U | 9/2019 |
| CN | 111446678 | A | 7/2020 |
| CN | 211704762 | U | 10/2020 |
| CN | 112237465 | A | 1/2021 |
| CN | 213993677 | U | 8/2021 |
| CN | 113331917 | A | 9/2021 |
| CN | 113456176 | A | 10/2021 |
| CN | 113712633 | A | 11/2021 |
| CN | 215273148 | U | 12/2021 |
| CN | 113907846 | A | 1/2022 |

OTHER PUBLICATIONS

International Search Report and Written Opinion issue in the International Patent Application No. PCT/CN2021/125624, dated Jan. 26, 2022 in 12 pages.

* cited by examiner

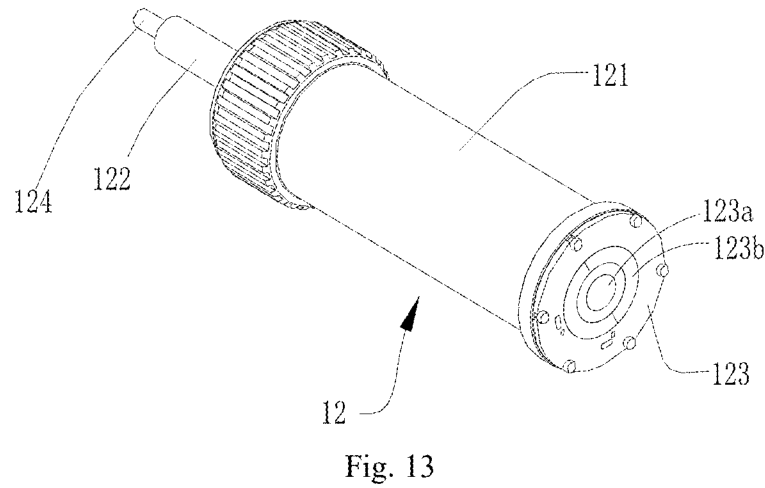
Fig. 13
129
123
128
121
1222
1223
1221
124
125
126
127
Fig. 14
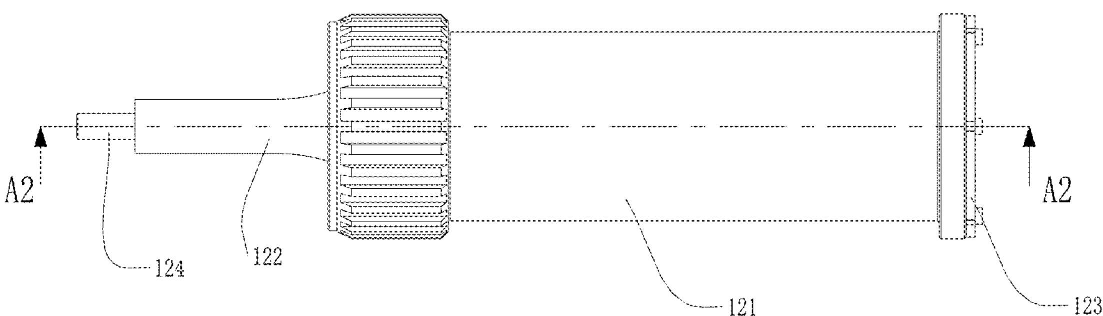
Fig. 15

ULTRASONIC SCALPEL HANDLE

CROSS-REFERENCE TO RELATED APPLICATIONS

This application is the U.S. National Phase under 35. U.S.C. § 371 of International Application PCT/CN2021/125624, filed Oct. 22, 2021, which claims priority to Chinese Patent Application No. 202011212999.8, filed Nov. 4, 2020, Chinese Patent Application No. 202120458579.1, filed Mar. 3, 2021, and Chinese Patent Application No. 202110756263.5, filed Jul. 5, 2021. The disclosures of the above-described applications are hereby incorporated by reference in their entirety.

FIELD OF TECHNOLOGY

The disclosure relates to the technical field of medical apparatus and instruments, and in particular, to a handle of an ultrasonic scalpel.

BACKGROUND

As a surgical equipment using ultrasonic energy, ultrasonic scalpel is used in various endoscopic surgery or conventional surgery, mainly for hemostatic separation or tissue coagulation of soft tissue. With the popularization of minimally invasive surgery, ultrasonic scalpel has become a conventional surgical instrument and is widely used.

Currently, the ultrasonic scalpel system on the market is mainly composed of a host with an ultrasonic generator, a handle, a cutting tool, and a transducer, wherein the transducer needs to be connected to a power supply by a power cord to obtain power source. The power cord is usually hung at the rear of the handle. On the one hand, during surgery, the power cord has a certain weight, and a greater gripping force is needed when the doctor holds the handle, which makes the doctor's hand tired and affecting the operation during surgery. On the other hand, during surgery, the power cord will rotate synchronously with the rotation of the transducer in the process of the rotation of the transducer to drive the cutting tool to change direction, thus causing the phenomenon of winding and knotting, which will also greatly affect the operation during surgery.

SUMMARY

The purpose of the disclosure is to provide a novel ultrasonic scalpel handle, to solve one or more problems in the prior art.

To achieve the above purpose, a technical solution employed by the disclosure is: an ultrasonic scalpel handle comprising a handle housing and a transducer assembly, wherein the handle housing has an accommodating cavity, the transducer assembly is integrally accommodated in the accommodating cavity and capable of rotating about its own axis in the accommodating cavity, the transducer assembly comprises a transducer shell and a transducer fixedly connected to each other, the transducer shell has a hollow cavity, at least a rear portion of the transducer is accommodated in the hollow cavity, the transducer assembly further comprises a conductive member fixedly provided outside the transducer shell, the conductive member at least has a conductive portion, the transducer is fixedly and electrically connected to the conductive portion, a power connecting member is fixedly arranged in the accommodating cavity of the handle housing, the power connecting member presses against the conductive portion, and throughout a process that the transducer assembly rotates about its own axis with respect to the handle housing, the power connecting member keeps in contact with the conductive portion to maintain electric connecting.

As a preferred embodiment, the conductive member is fixedly disposed on an outer circumference of the transducer shell, the conductive portion is in a shape of a ring, an axis of the conductive portion and an axis of the transducer assembly are collinear, the power connecting member is located on a circumferential outer side of the transducer assembly, and the power connecting member presses against the conductive portion inward in a radial direction of the transducer shell.

Further, the conductive portion comprises a first conductive portion and a second conductive portion which are insulated from each other and are in a shape of a ring, the transducer has a first electric lead and a second electric lead, the first electric lead is electrically connected to the first conductive portion, and the second electric lead is electrically connected to the second conductive portion; the power connecting member has a first power connecting member and a second power connecting member arranged independently with each other, the first power connecting member presses against the first conductive portion, and the second power connecting member presses against the second conductive portion.

In some embodiments, the first conductive portion and the second conductive portion are disposed at intervals in an axis direction of the transducer shell, and the first power connecting member and the second power connecting member are disposed at intervals in a front-rear direction of the handle housing.

In some embodiments, the power connecting member comprises two conductive rings both made of conductive materials, a spacing ring located between the two conductive rings in an axis direction and made of insulating materials, the two conductive rings and the spacing ring are fixedly sleeved on an outer circumference of the handle housing, and the first conductive portion and the second conductive portion are composed of the two conductive rings, respectively.

In some embodiments, the conductive member is fixedly disposed on a rear end portion of the transducer shell, and the power connecting member elastically presses against the conductive portion forward in the front-rear direction of the transducer shell.

Further, the conductive portion comprises a first conductive portion and a second conductive portion insulated from each other, the first conductive portion and the second conductive portion are in a shape of a disc or ring taking the axis of the transducer assembly as a rotation center, the transducer has a first electric lead and a second electric lead, the first electric lead is electrically connected to the first conductive portion, and the second electric lead is electrically connected to the second conductive portion;

the power connecting member has a first elastic power connecting member and a second elastic power connecting member arranged independently with each other, the first elastic power connecting member and the second elastic power connecting member are both elastic pieces made of metal materials, an end portion of the first elastic power connecting member and an end portion of the second elastic power connecting member are fixedly disposed in the handle housing, respectively, the other end portion of the first elastic power connecting member presses against the first conductive portion forward, and the other end portion of the second elastic power connecting member presses against the second conductive portion forward.

In some embodiments, the conductive member comprises a plate body, a first conductive piece and a second conductive piece which are fixed on the plate body and made of metal materials, the first conductive portion is composed by the first conductive piece, the second conductive portion is composed by the second conductive piece, the first elastic power connecting member presses against a rear side of the first conductive piece, and the second elastic power connecting member presses against a rear side of the second conductive piece.

In some embodiments, the second conductive portion is in a shape of a ring and circumferentially disposed on a circumferential outer side of the first conductive portion, and the first conductive portion and the second conductive portion are disposed at intervals in a radial direction of the plate body.

In some embodiments, the ultrasonic scalpel handle further comprises a power cord, an end portion of the power cord is fixedly connected to the power connecting member in the accommodating cavity, and the other end portion of the power cord goes through the accommodating cavity and goes out from a lower portion of the handle housing.

Due to the use of the above technical solutions, the disclosure has the following advantages over conventional art: in the ultrasonic scalpel handle of the disclosure, the transducer assembly is completely accommodated in the handle housing, the conductive member is arranged outside the transducer shell, and the power connecting member is arranged in the handle housing, such that the power connecting member presses against the conductive portion of the conductive member, and in the process that the transducer assembly rotates about its own axis with respect to the handle housing, the power connecting member is always in contact with the conductive portion to maintain electric connecting. In this way, in the process that the transducer assembly rotates about its own axis in the handle housing, power cord does not rotate with it, and the power cord may further extend in the lower part of the handle, such that a series of problems of heavy burden on the arm and easy fatigue, and knotting of the power cord, etc. caused by the power cord extending from the rear portion of the handle housing are avoided.

BRIEF DESCRIPTION OF THE DRAWINGS

FIG. 13 is a schematic overall structure diagram of the transducer assembly according to Embodiment 2 of the disclosure;

FIG. 14 is a schematic exploded structure diagram of the transducer assembly shown in FIG. 13;

FIG. 15 is a front view of the transducer assembly shown in FIG. 13;

REFERENCE NUMBERS

- 1—ultrasonic scalpel handle; 11—handle housing; 11*a*—left housing; 11*b*—right housing; 11*c*—top cover; 11*d*—viewing window;
- 12—transducer assembly; 121—transducer shell; 1211—front shell; 1212—rear shell; 1213—middle shell; 121*a*—straight-tooth ring;
- 122—transducer; 1221—horn shaft; 1222—horn core; 1223—retaining ring; 1224—first electric lead/second electric lead;
- 123—conductive member; 1231—first conductive ring (first conductive portion); 1232—second conductive ring (second conductive portion); 1233—spacing ring; 1234—insulating sleeve; 1235—positioning projection; 1230—plate body; 123*a*—first conductive piece; 123*b*—second conductive piece; 123*c*—first through hole; 123*d*—second through hole;
- 124—connecting screw; 125—rubber gasket; 126—rubber ring; 127—front retaining cover; 128—rear sealing ring; 129—screw;
- 13—power connecting member; 131—first power connecting member; 132—second power connecting member; 13*a*—first elastic power connecting member; 13*b*—second elastic power connecting member;
- 2—cutting tool; 3—power adapter; 31—connecting wire; 4—pedal switch; 5—socket.

DETAILED DESCRIPTION OF EXEMPLARY EMBODIMENTS

For conveniently describing the relative positions of the components in the ultrasonic scalpel, the above and following descriptions of the front-rear direction are defined with reference to the direction observed by the operator while holding the ultrasonic scalpel for operation, where the position of the ultrasonic scalpel acting on the surgical site is front, and the position of the ultrasonic scalpel near the human body is rear.

Figure 1:
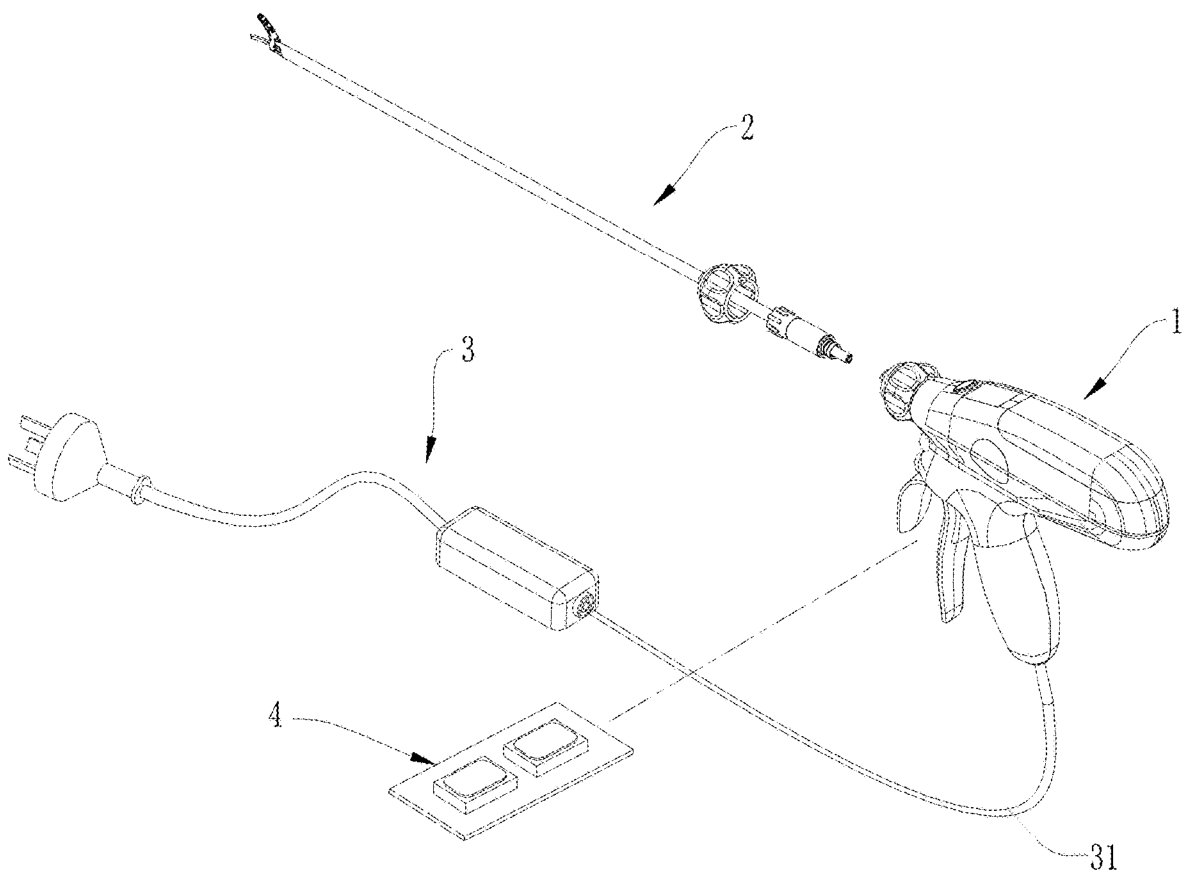
FIG. 1 is a schematic structure diagram of an ultrasonic scalpel system according to the disclosure.
Figure 2:
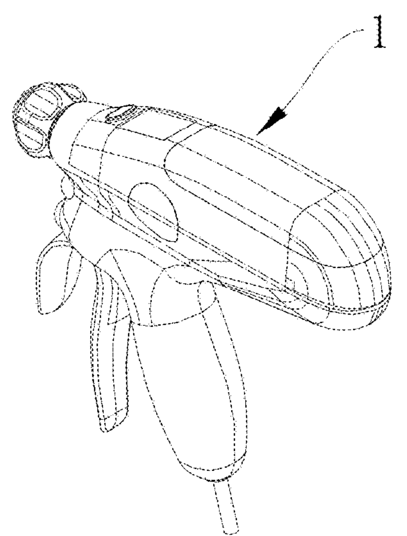
FIG. 2 is a schematic overall structure diagram of the ultrasonic scalpel handle according to Embodiment 1 of the disclosure.

Referring to the ultrasonic scalpel system shown in FIG. 1, it comprises an ultrasonic scalpel, and a power adapter 3 for supplying energy to the ultrasonic scalpel. A pedal switch 4 is optionally provided for operating control such as turning the ultrasonic scalpel on and off. Wherein the ultrasonic scalpel comprises an ultrasonic scalpel handle 1, and a cutting tool 2 detachably mounted on the ultrasonic scalpel handle 1.

Referring to the figs, the ultrasonic scalpel handle 1 comprises a handle housing 11 and a transducer assembly 12, the handle housing 11 comprises a left housing 11*a* and a right housing 11*b* that are fixedly connected and fitted with each other, and a top cover 11*c* at the top, which has an accommodating cavity, wherein the transducer assembly 12 is integrally accommodated in the accommodating cavity and can rotate about its own axis in the accommodating cavity, wherein the axis of the transducer assembly 12 extends in the front-rear direction. The transducer assembly 12 comprises a transducer shell 121 and a transducer 122 fixedly connected to each other, the transducer shell 121 has a hollow cavity, and at least a rear portion of the transducer 122 is accommodated in the hollow cavity and is fixed to the transducer shell 121.

Specifically, referring to the figs, the transducer 122 is an one-piece member, and comprises a horn shaft 1221 and a horn core 1222 successively arranged in the axis direction, a retaining ring 1223 is formed at a position of the connection between the horn shaft 1221 and the horn core 1222, the horn core 1222 and the retaining ring 1223 are both accommodated in the hollow cavity of the transducer shell 121, and the front portion of the horn shaft 1221 extends out the hollow cavity and is connected to a cutting tool 2 via a connecting screw 124 of the front portion.

The transducer assembly 12 further comprises a conductive member 123 fixedly arranged outside the transducer shell 121, the conductive member 123 has at least a conductive portion, the transducer 122 is fixedly and electrically connected to the conductive portion, an power connecting member 13 is further fixedly arranged in the accommodating cavity of the handle housing 11, the power connecting member 13 presses against the conductive portion, and in the process that the transducer 122 rotates about its own axis with respect to the handle housing 11, the power connecting member 13 is always in contact with the conductive portion to maintain electric connecting.

In the following, the technical solution of the disclosure is further described combining with the accompanying figs and two specific embodiments.

Embodiment 1

As shown in FIG. 2 to FIG. 10, the conductive member 123 is fixedly disposed on the outer circumference of the transducer shell 121, the conductive portion 123 is in the shape of a ring, and the axis of the conductive portion and the axis of the transducer assembly 12 are collinear. Specifically, the conductive portion comprises a first conductive portion and a second conductive portion insulated from each other, the transducer 122 has two electric leads 1224, namely a first electric lead and a second electric lead, and the two electric leads are electrically connected to the two conductive portions, respectively.

The two conductive portions are disposed at intervals in the axis direction of the transducer shell 121, in this embodiment, as shown in FIG. 5 to FIG. 10, the conductive portion 123 comprises two conductive rings, namely a first conductive ring 1231 and a second conductive ring 1232, both made of conductive materials, and a spacing ring 1233 arranged between the first conductive ring 1231 and the second conductive ring 1232 and made of insulating material, the first conductive ring 1231 forms the first conductive portion and the second conductive ring 1232 forms the second conductive portion. An end portion of the first electric lead 1224 is fixedly arranged on the first conductive ring 1231 to achieve electric connecting, and an end portion of the second electric lead 1224 is fixedly arranged on the second conductive portion 1232 to achieve electric connecting.

The first conductive ring 1231, the second conductive portion 1232 and the spacing ring 1233 are fixedly sleeved on the outer circumference of the transducer shell 121, specifically, between each conductive ring and the spacing ring 1233, a circumferential limiting structure for limiting relative rotation is provided between the two, and a positioning structure for limiting the rotation of the conductive member 123 and limiting the movement of the conductive member 123 in the axis direction is provided between the whole conductive member 123 and the transducer shell 121.

Figure 6:
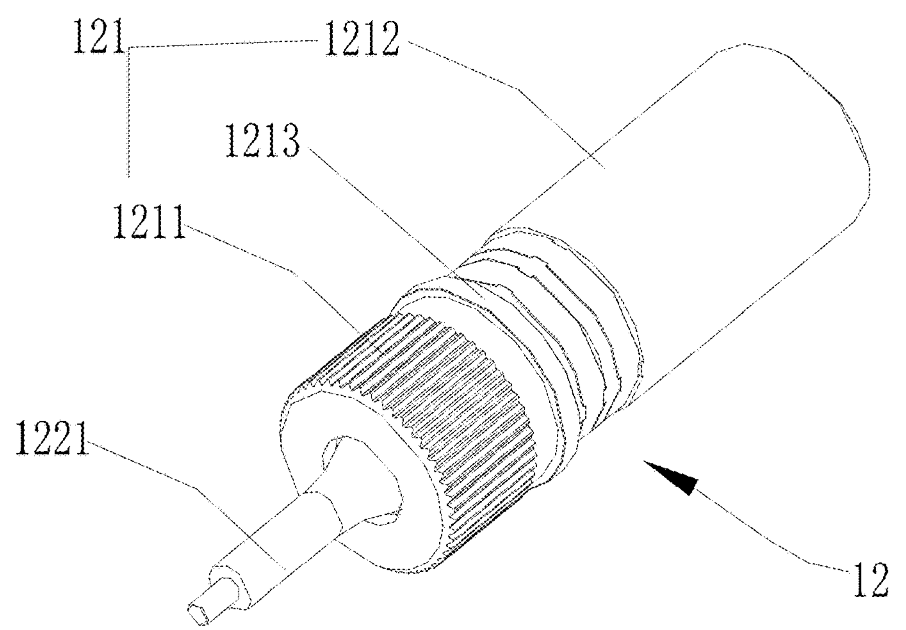
FIG. 6 is a schematic overall structure diagram of the transducer assembly according to Embodiment 1 of the disclosure.
Figure 7:
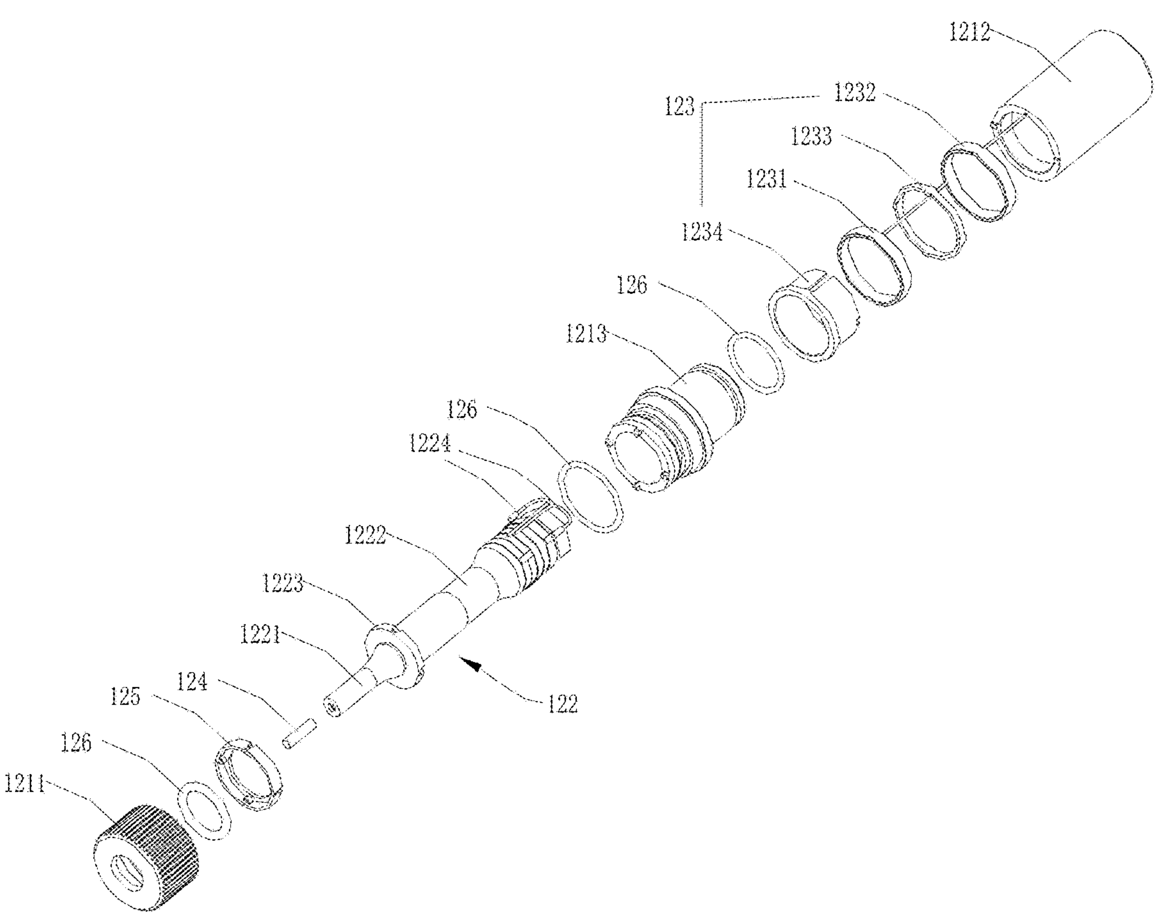
FIG. 7 is a schematic exploded structure diagram of the transducer assembly shown in FIG. 6.
Figure 8:
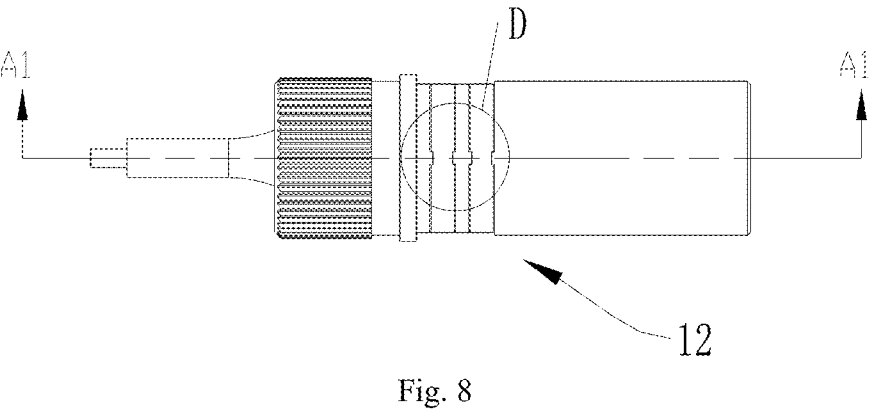
FIG. 8 is a front view of the transducer assembly shown in FIG. 6.
Figure 9:
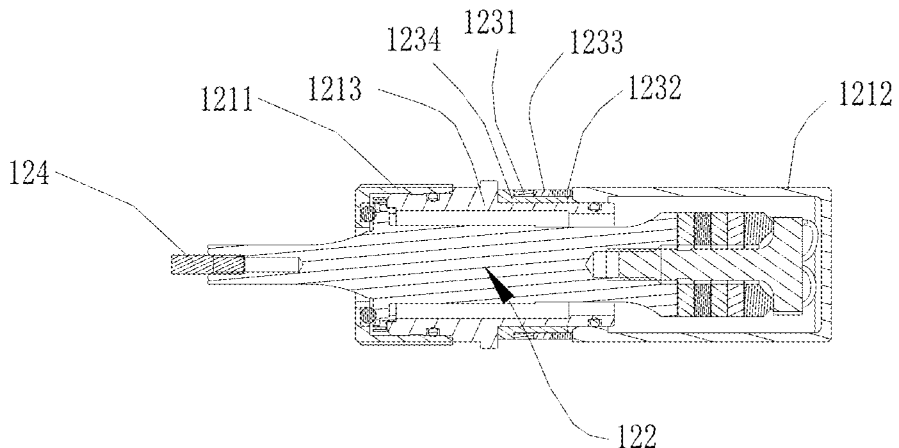
FIG. 9 is a sectional view along Line A1-A1 in FIG. 8.
Figure 10:
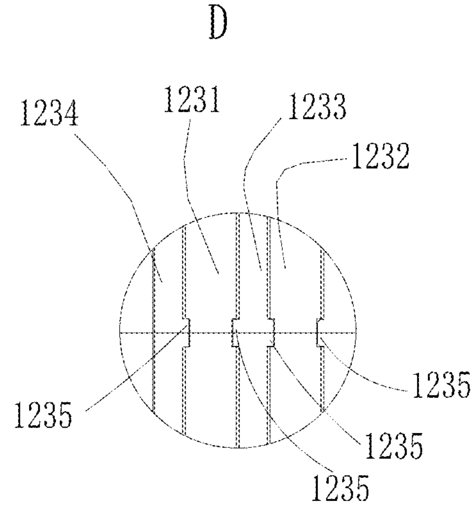
FIG. 10 is an enlarged diagram at Part D in FIG. 8.

Here, referring to FIG. 6 and FIG. 7, the transducer shell 121 comprises a front shell 1211, a middle shell 1213 and a rear shell 1212 successively disposed in the front-rear direction, a rubber gasket 125 and a rubber ring 126 are provided between the front shell 1211 and the middle shell 1213 to achieve sealing, and a rubber ring 126 is arranged between the middle shell 1213 and the rear shell 1212 to achieve sealing, to seal the transducer 122 accommodated in the transducer shell 121 in the transducer shell 121. The conductive member 123 is fixedly mounted on the middle shell 1213 and located on the front side of the rear shell 1212.

The conductive member 123 further comprises an insulating sleeve 1234, the insulating sleeve 1234 is fixedly sleeved on the outer circumference of the middle shell 1213, the first conductive ring 1231, the spacing ring 1233 and the second conductive ring 1232 are sleeved on the outer circumference of a rear tube section of the insulating sleeve 1234 together, and the front portion of the first conductive ring 1231 and the insulating sleeve 1234, the rear portion of the first conductive ring 1231 and the front portion of the spacing ring 1233, the rear portion of the spacing ring 1233 and the front portion of the second conductive ring 1232, and the rear portion of the second conductive ring 1232 and the front portion of the rear shell 1212 are fitted and positioned to each other in a manner of positioning projections 1235 and recesses, in this way, the conductive member 123 is fixedly on the transducer shell 121.

Figure 3:
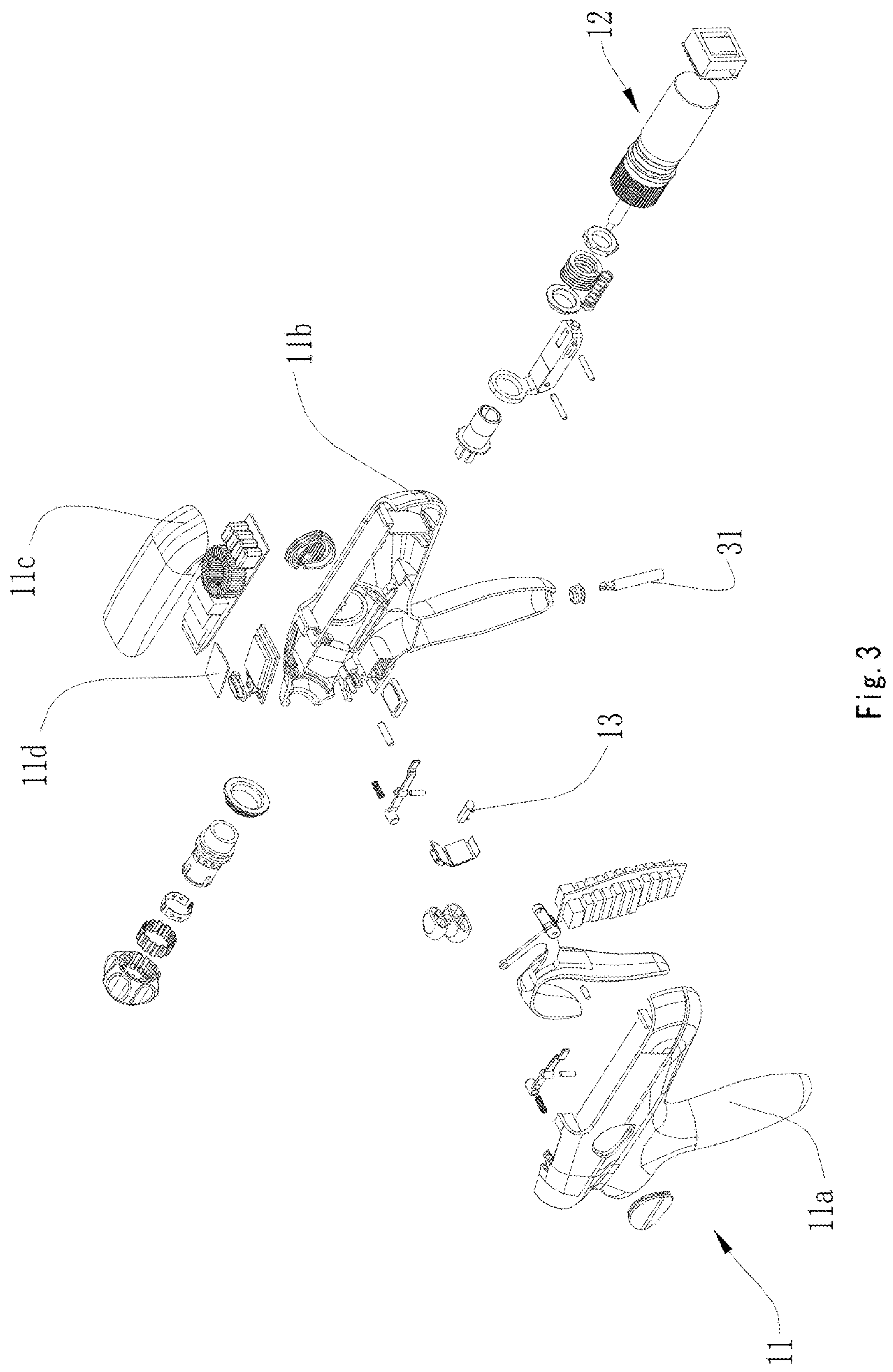
FIG. 3 is a schematic exploded structure diagram of the ultrasonic scalpel handle according to Embodiment 1 of the disclosure.
Figure 4:
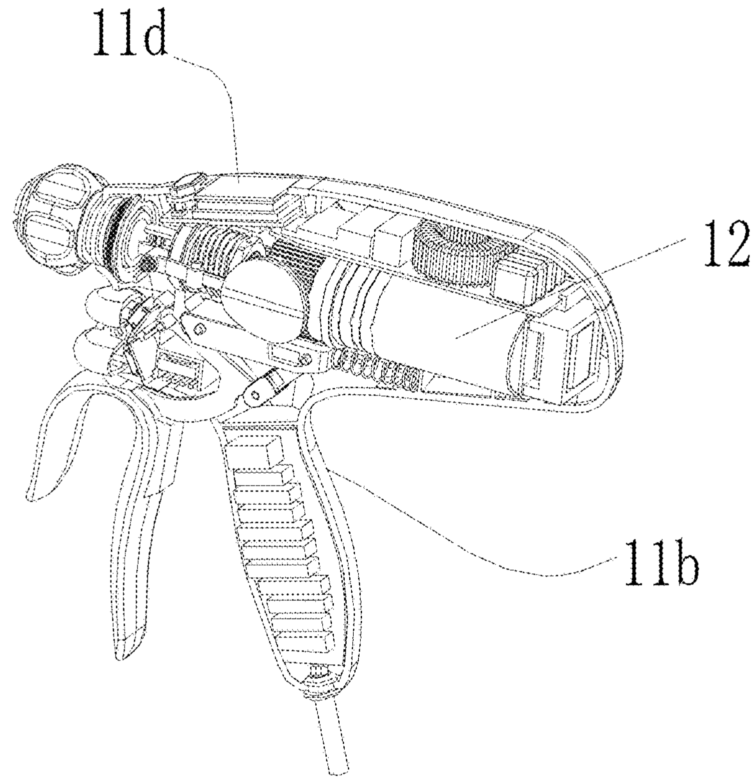
FIG. 4 is a schematic inner structure diagram of the ultrasonic scalpel handle according to Embodiment 1 of the disclosure.
Figure 5:
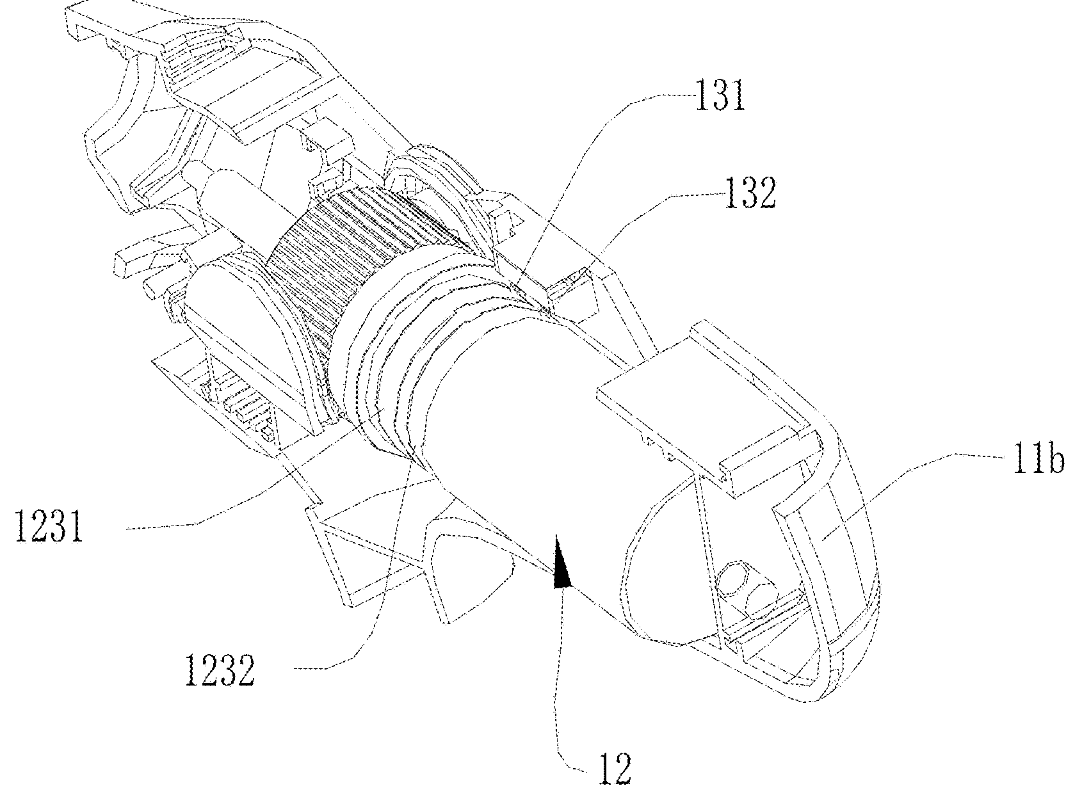
FIG. 5 is a schematic diagram of the connection between the transducer assembly and the power connecting member of the ultrasonic scalpel handle according to Embodiment 1 of the disclosure.

Referring to FIG. 3 and FIG. 5, the handle housing 11 is further provided with an power connecting member 13, the power connecting member 13 is located on the circumferential outer side of the transducer assembly 12, and the power connecting member 13 presses against the outer circumference of the transducer shell 121 and contacts the conductive portion, specifically, the power connecting member 13 has a first power connecting member 131 and a second power connecting member 132 arranged independently with each other, the first power connecting member 131 and the second power connecting member 132 are both made of metal material and have certain elasticity in their own length direction, the two are disposed at intervals in the front-rear direction of the handle housing 11, the first power connecting member 131 elastically presses against the outer circumference of the first conductive ring 1231 inward in the radial direction of the transducer shell 121, and the second power connecting member 132 elastically presses against the outer circumference of the second conductive ring 1232 inward in the radial direction of the transducer shell 121. In the process that the transducer assembly 12 rotates about its own axis with respect to the handle housing 11, and the first power connecting member 131 is always in contact with the first conductive ring 1231 and the second power connecting member 132 is always in contact with the second conductive ring 1232 to maintain electric connecting Referring to FIG. 5, in this embodiment, the power connecting member 13 is arranged in the handle housing 11 and located at the upper position, and above the transducer assembly 12, such that the power connecting member 13 can press against the outer circumference of the transducer assembly 12 downward to maintain electric connecting more stably.

In this way, it only needs to connect two leads of the power cord to the first power connecting member 131 and the second power connecting member 132 inside the handle housing 11, respectively, then the power cord can go out from the lower portion of the handle housing 11 to connect the power supply, in this way, in the process that the transducer assembly 12 rotates about its own axis in the handle housing 11, the power cord does not rotate with it, such that a series of problems of heavy burden on the arm and easy fatigue, and knotting of the power cord, etc. caused by the power cord extending from the rear portion of the handle housing 11 are avoided.

Embodiment 2

Referring to FIG. 11 to FIG. 19, in this embodiment, the conductive member 123 is fixedly disposed on the rear end portion of the transducer shell 121, and the rear end portion of the transducer shell 121 is arranged open, and the conductive member 123 closes the transducer shell 121 from the rear end. The conductive portion is disposed on the rear portion of the conductive member 123, the power connecting member 13 is arranged in the handle housing 11 and located behind the transducer assembly 12, and the power connecting member 13 elastically presses against the conductive portion forward.

Specifically, the conductive portion comprises a first conductive portion and a second conductive portion which are insulated from each other, the transducer 122 has two electric leads, namely a first electric lead and a second electric lead (not shown), and the first electric lead is electrically connected to the first conductive portion, and the second electric lead is electrically connected to the second conductive portion. The power connecting member 13 has a first elastic power connecting member 13*a* and a second elastic power connecting member 13*b* arranged independently with each other and insulated from each other, the first elastic power connecting member 13*a* presses against the first conductive portion, and the second elastic power connecting member 13*b* presses against the second conductive portion. The above first conductive portion and the second conductive portion are in the shape of a disc or ring taking the axis of the transducer assembly 12 as a rotation center, in this way, in the process that the transducer assembly 12 rotates about its own axis, the first elastic power connecting member 13*a* and the second elastic power connecting member 13*b* can keep to press against the first conductive portion and the second conductive portion respectively.

In this embodiment, the conductive member 123 comprises a plate body 1230, and a first conductive piece 123*a* and a second conductive piece 123*b* which are fixed on the plate body 1230 and made of metal materials, wherein, the first conductive piece 123*a* is in the shape of a disc, and the second conductive piece 123*b* is in the shape of a ring and circumferentially disposed on the circumferential outer side of the first conductive piece 123*a*, and the first conductive piece 123*a* and the second conductive piece 123*b* are disposed at intervals in the radial direction of the conductive member 123, that is, the outer circumferential edge of the first conductive piece 123*a* and the inner circumferential edge of the second conductive piece 123*b* have a distance in the radial direction of the conductive member 123. The first conductive piece 123*a* forms the first conductive portion, and the second conductive piece 123*b* forms the second conductive portion.

A first through hole 123*c* and a second through hole 123*d* are opened on the plate body 1230 penetrating in its own thickness direction, the first electric lead runs through the first through hole 123*c* and is fixed to the first conductive piece 123*a* by means of welding to achieve electric connecting, and the second electric lead runs through the second through hole 123*d* and is fixed to the second conductive piece 123*b* by means of welding to achieve electric connecting.

Figures 11, 12:
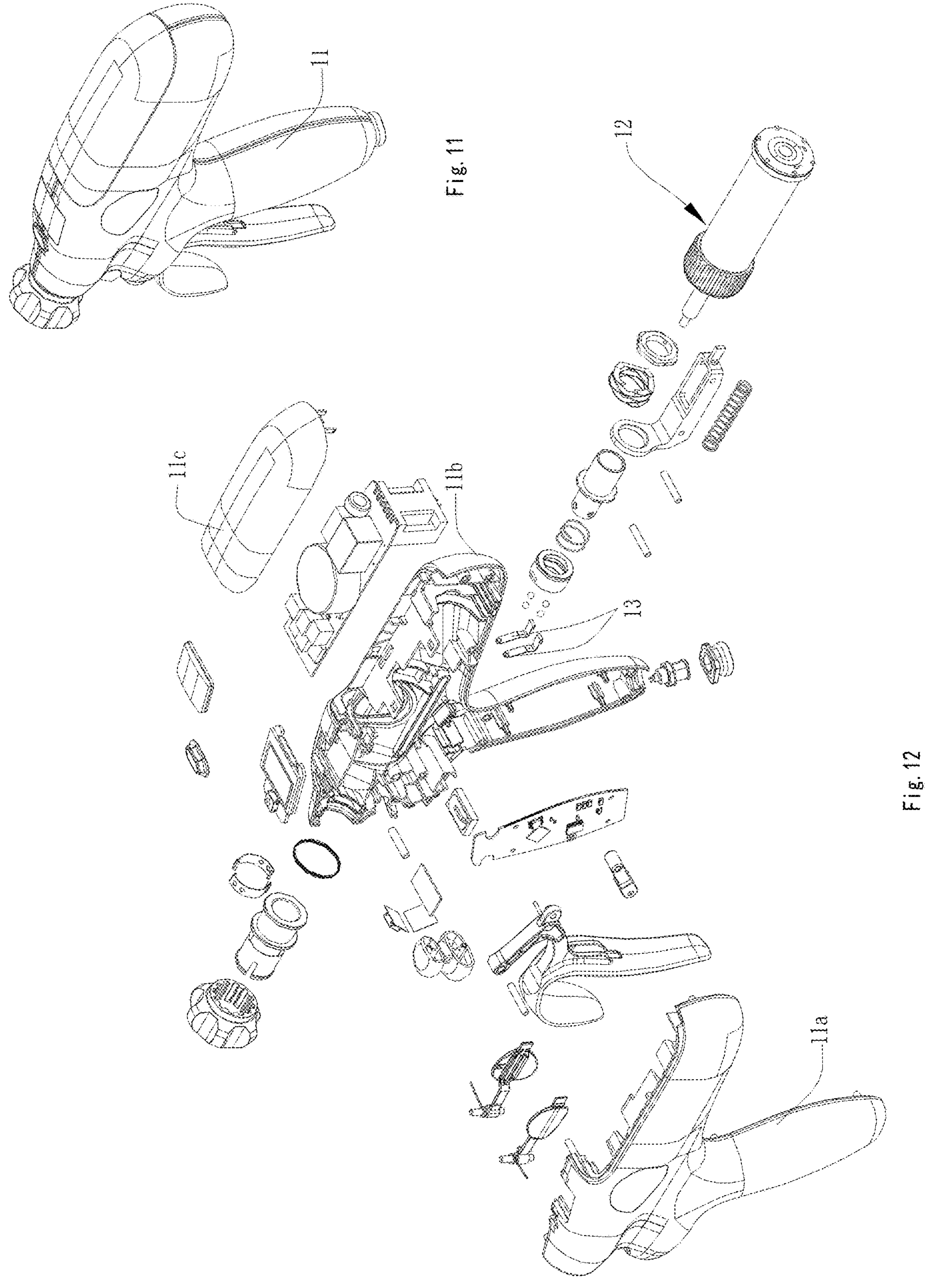
FIG. 11 is a schematic overall structure diagram of the ultrasonic scalpel handle according to Embodiment 2 of the disclosure.
FIG. 12 is a schematic exploded structure diagram of the ultrasonic scalpel handle according to Embodiment 2 of the disclosure.
Figure 16:
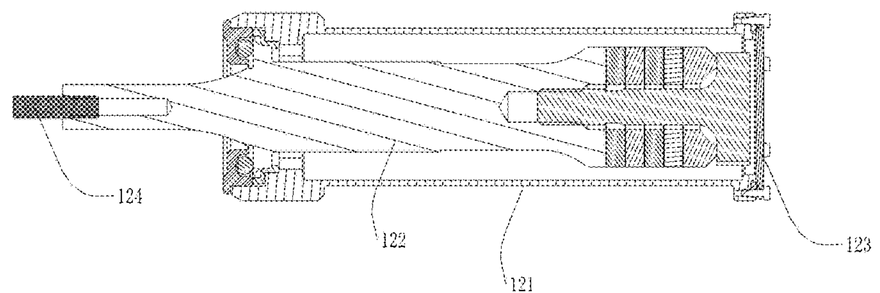
FIG. 16 is a sectional view along Line A2-A2 in FIG. 15.
Figure 17:
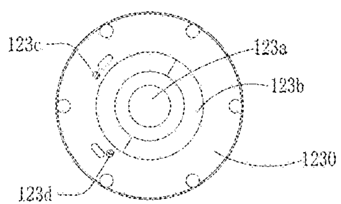
FIG. 17 is a left view of the transducer assembly shown in FIG. 13.
Figure 18:
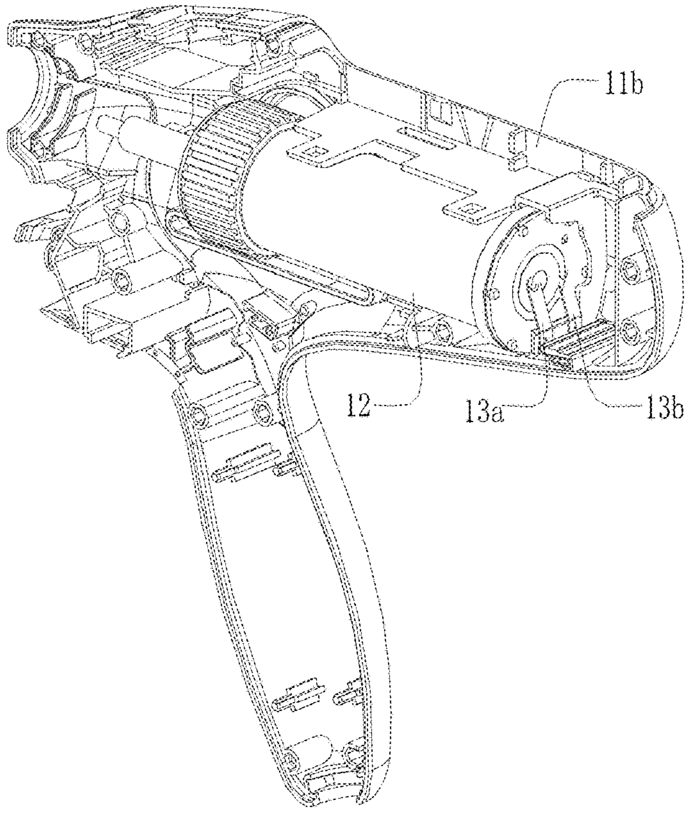
FIG. 18 is a schematic diagram of the connection between the transducer assembly and the power connecting member according to Embodiment 2 of the disclosure.
Figure 19:
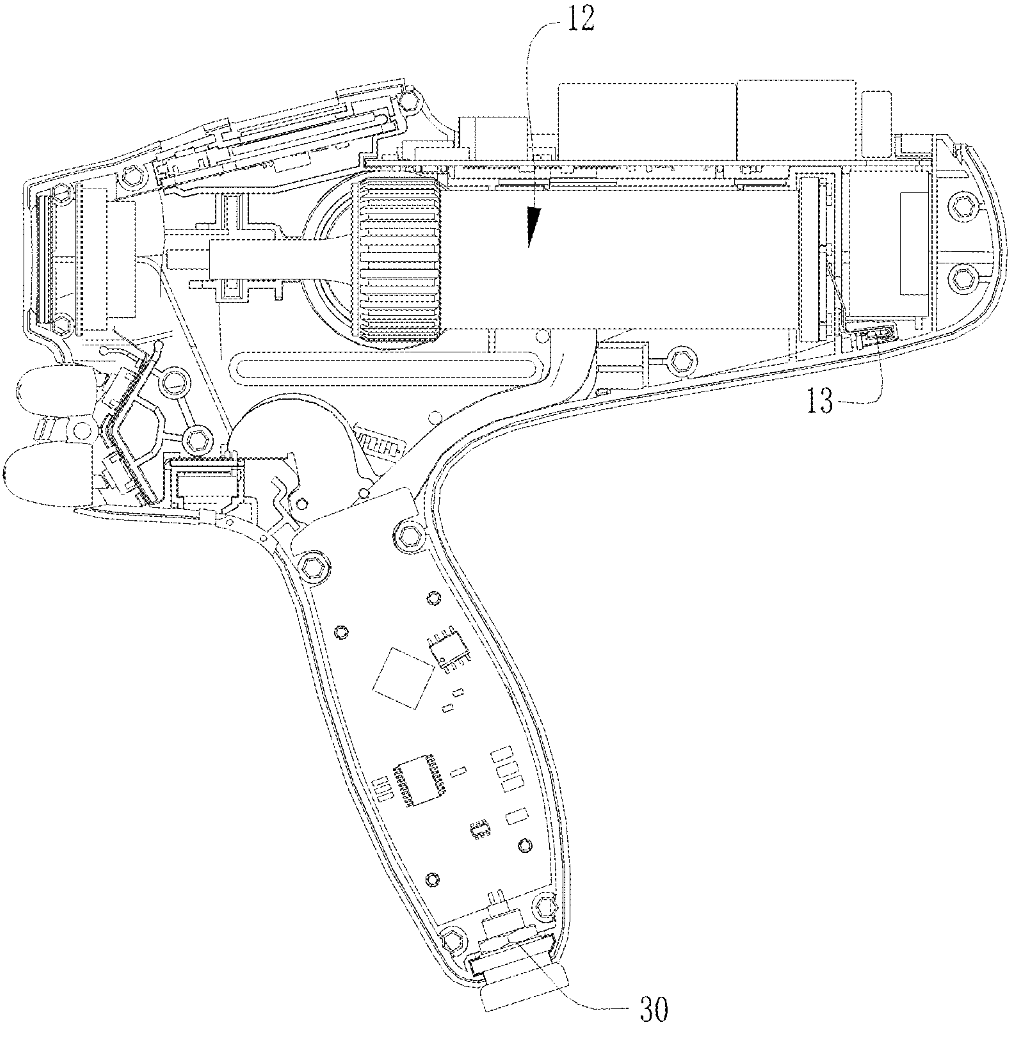
FIG. 19 is a schematic inner structure diagram of the ultrasonic scalpel handle of the disclosure.

Referring to FIG. 12 and FIG. 18, the first elastic power connecting member 13*a* and the second elastic power connecting member 13*b* are both elastic pieces made of metal materials, the lower end portion of the first elastic power connecting member 13*a* and the lower end portion of the second elastic power connecting member 13*b* are fixedly disposed in the handle housing 11 respectively, the upper end portion of the first elastic power connecting member 13*a* presses against the rear side of the first conductive portion 123*a* forward, and the upper end portion of the second elastic power connecting member 13*b* presses against the rear side of the second conductive portion 123*b* forward.

Referring to FIG. 12, the ultrasonic scalpel handle further comprises a power cord, the power cord comprises a conductive wire (not shown) located in the accommodating cavity, and a socket fixedly disposed on the lower portion of the handle housing 11, and there are two conductive wires, the two conductive wires are fixedly connected at one end to the first elastic power connecting member 13*a* and the second elastic power connecting member 13*b* respectively, and the two conductive wires are fixedly and electrically connected at the other end to the socket 5, and a connecting wire 31 of the power adapter 3 can fitted and connected to the socket 5 via a plug thereon (not shown).

In this way, it only needs to connect the two conductive wires of the power cord to the first elastic power connecting member 13*a* and the second elastic power connecting member 13*b* respectively, then the power cord can go out from the lower portion of the handle housing 11 to connect the power supply, in this way, in the process that the transducer assembly 12 rotates about its own axis in the handle housing 11, the power cord does not rotate with it, such that a series of problems of heavy burden on the arm and easy fatigue, and knotting of the power cord, etc. caused by the power cord extending from the rear portion of the handle housing 11 are avoided.

The embodiments described above are only for illustrating the technical concepts and features of the disclosure, and are intended to make those skilled in the art being able to understand the disclosure and thereby implement it, and should not be concluded to limit the protective scope of this disclosure. Any equivalent variations or modifications according to the disclosure should be covered by the protective scope of the disclosure.

I claim:

1. An ultrasonic scalpel handle comprising a handle housing having an accommodating cavity and a transducer assembly, the transducer assembly integrally accommodated in the accommodating cavity and configured to rotate about an axis of the transducer assembly in the accommodating cavity, wherein the transducer assembly comprises a transducer shell and a transducer fixedly connected to each other, the transducer shell comprises a hollow cavity, and at least a rear portion of the transducer is accommodated in the hollow cavity, wherein the transducer assembly further comprises a conductive member fixedly provided outside the transducer shell, the conductive member comprises a conductive portion, and the transducer is fixedly and electrically connected to the conductive portion, wherein a power connecting member is fixedly arranged in the accommodating cavity of the handle housing, the power connecting member presses against the conductive portion, and with the transducer assembly rotating about the axis with respect to the handle housing, the power connecting member keeps in contact with the conductive portion to maintain electrical connection, wherein the conductive member is fixedly disposed on a rear end portion of the transducer shell, the power connecting member is an elastic element comprising a conductive material, and the power connecting member presses elastically against the conductive portion and forwardly along a front-rear direction of the transducer shell, wherein a power cord connects a lower portion of the handle housing to a power supply, the power cord is, when the ultrasonic scalpel handle is handled for an operation, disposed below the power connecting member and the transducer assembly and extends downwardly out from the handle in a direction that is different from the axis of the transducer assembly, wherein the conductive portion comprises a first conductive portion and a second conductive portion insulated from each other, at least one of the first conductive portion or the second conductive portion is in a shape of a disc or a ring and is configured to rotate about the axis of the transducer assembly, wherein the transducer comprises a first electric lead and a second electric lead, the first electric lead is electrically connected to the first conductive portion, and the second electric lead is electrically connected to the second conductive portion, wherein the power connecting member comprises a first elastic power connecting member and a second elastic power connecting member arranged independently from each other, the first elastic power connecting member and the second elastic power connecting member are both elastic pieces comprising metal materials configured to flex in the front-rear direction, wherein an end portion of the first elastic power connecting member and an end portion of the second elastic power connecting member are fixedly disposed in the handle housing, another end portion of the first elastic power connecting member presses against the first conductive portion forwardly, and another end portion of the second elastic power connecting member presses against the second conductive portion forwardly, wherein the conductive member comprises a plate body, a first conductive piece, and a second conductive piece, the first conductive piece and the second conductive piece are fixed on the plate body and comprise metal materials, the first conductive portion comprises the first conductive piece, the second conductive portion comprises the second conductive piece, and wherein, the first elastic power connecting member flexes backward to press forwardly against a rear side of the first conductive piece, and the second elastic power connecting member flexes backward to press forwardly against a rear side of the second conductive piece.

2. The ultrasonic scalpel handle according to claim 1, wherein the second conductive portion is in a shape of a ring and circumferentially disposed on a circumferential outer side of the first conductive portion, and the first conductive portion and the second conductive portion are disposed at intervals in a radial direction of the plate body.

3. The ultrasonic scalpel handle according to claim 1, wherein an end portion of the power cord is fixedly connected to the power connecting member in the accommodating cavity, and another end portion of the power cord goes through the accommodating cavity and goes out from the lower portion of the handle housing.

4. The ultrasonic scalpel handle according to claim 1, wherein the ultrasonic scalpel handle further comprises a socket fixedly disposed on the lower portion of the handle housing, wherein the power cord comprises a conductive wire located in the accommodating cavity, and wherein an end portion of the conductive wire is fixedly and electrically connected to the power connecting member, and another end portion of the conductive wire is fixedly and electrically connected to the socket.

5. The ultrasonic scalpel handle according to claim 1, wherein the first elastic power connecting member or the second elastic power connecting member comprises a cantilever structure with a fixed end and a free end, the cantilever structure elongated in a direction that is different from the axis of the transducer assembly and configured to flex in the front-rear direction, wherein the fixed end corresponds to the end portion of the first elastic power connecting member or the end portion of the second elastic power connecting member, and wherein the free end corresponds to the another end portion of the first elastic power connecting member or the another end portion of the second elastic power connecting member.

6. The ultrasonic scalpel handle according to claim 1, wherein, as the plate body rotates about the axis of the transducer assembly, the first elastic power connecting member slides against and maintains contact with a rear side of the first conductive piece by pressing forwardly, and the second elastic power connecting member slides against and maintains contact with a rear side of the second conductive piece by pressing forwardly.

* * * * *